(12) United States Patent
Krattiger

(10) Patent No.: US 9,726,878 B2
(45) Date of Patent: Aug. 8, 2017

(54) EYEPIECE

(71) Applicants: Karl Storz GmbH & Co. KG, Tuttlingen (DE); Storz Endoskop Produktions GmbH, Tuttlingen (DE)

(72) Inventor: Beat Krattiger, Beringen (CH)

(73) Assignees: Karl Storz GmbH & Co. KG, Tuttlingen (DE); Storz Endoskop Produktions GmbH, Tuttlingen (DE)

(*) Notice: Subject to any disclaimer, the term of this patent is extended or adjusted under 35 U.S.C. 154(b) by 0 days.

(21) Appl. No.: 14/491,700

(22) Filed: Sep. 19, 2014

(65) Prior Publication Data

US 2015/0085355 A1    Mar. 26, 2015

(30) Foreign Application Priority Data

Sep. 20, 2013 (DE) .......... 10 2013 110 425

(51) Int. Cl.
*G02B 21/00* (2006.01)
*A61B 1/00* (2006.01)
*G02C 7/08* (2006.01)
*G02B 23/24* (2006.01)
*G02B 25/00* (2006.01)
*G02B 27/00* (2006.01)
*A61B 34/30* (2016.01)

(52) U.S. Cl.
CPC ........ *G02B 25/001* (2013.01); *A61B 1/00195* (2013.01); *A61B 34/30* (2016.02); *G02B 21/0012* (2013.01); *G02B 23/2453* (2013.01); *G02B 27/0025* (2013.01); *G02C 7/081* (2013.01)

(58) Field of Classification Search
CPC .............. G02B 25/001; G02B 27/0025; G02B 21/0012; G02B 23/2453; G02C 7/081; A61B 1/00195; A61B 19/2203
USPC .......... 359/368, 434, 643; 600/163; 606/130
See application file for complete search history.

(56) References Cited

U.S. PATENT DOCUMENTS

| 4,217,048 A | 8/1980 | Egawa |
| 4,916,534 A * | 4/1990 | Takhashi ............ A61B 1/00096 348/337 |
| 4,936,667 A * | 6/1990 | Rohr et al. .................... 359/480 |
| 5,341,240 A | 8/1994 | Broome |
| 5,455,643 A * | 10/1995 | Ki-Ho ........................... 351/203 |

(Continued)

FOREIGN PATENT DOCUMENTS

| DE | 52241 C | 8/1889 |
| DE | 202007011682 U1 | 2/2008 |

(Continued)

OTHER PUBLICATIONS

Arines, Justo, et al. "Adaptive Astigmatism-Correcting Device for Eyepieces", Academnt of Optometry, Optometry and Vision Science, vol. 88, No. 12, Dec. 2011, pp. 1524-1528.

(Continued)

*Primary Examiner* — Frank Font
(74) *Attorney, Agent, or Firm* — Whitmyer IP Group LLC

(57) ABSTRACT

An eyepiece includes a focusing apparatus for positioning the area perceived as in focus by the relaxed human eye and for correcting axial ametropia of an eye of a user of the eyepiece and a correction apparatus for adjustable correction of an astigmatism of an eye of a user of the eyepiece.

14 Claims, 3 Drawing Sheets

(56) References Cited

U.S. PATENT DOCUMENTS

| | | | | |
|---|---|---|---|---|
| 6,069,651 | A * | 5/2000 | Tsuyuki | G02B 23/2484 348/65 |
| 8,820,931 | B2 * | 9/2014 | Walsh | A61B 3/102 351/206 |
| 9,316,834 | B2 * | 4/2016 | Makino | G02B 27/0172 |
| 9,420,949 | B2 * | 8/2016 | Van Heugten | A61F 9/007 |
| 9,492,079 | B2 * | 11/2016 | Walsh | A61B 3/102 |
| 2002/0105730 | A1 * | 8/2002 | Clark | 359/675 |
| 2005/0119529 | A1 | 6/2005 | Farr et al. | |
| 2006/0103947 | A1 * | 5/2006 | Shinohara | G02B 3/14 359/687 |
| 2008/0285043 | A1 * | 11/2008 | Fercher et al. | 356/451 |
| 2009/0019758 | A1 * | 1/2009 | Baugher | 42/111 |
| 2009/0257065 | A1 * | 10/2009 | Hauger et al. | 356/479 |
| 2012/0147460 | A1 * | 6/2012 | Kubler et al. | 359/389 |
| 2014/0002587 | A1 * | 1/2014 | Aguren | H04N 13/044 348/36 |
| 2014/0176909 | A1 * | 6/2014 | Spivey | A61B 3/04 351/223 |
| 2014/0226126 | A1 * | 8/2014 | Irnleitner | 351/159.52 |

FOREIGN PATENT DOCUMENTS

| | | | |
|---|---|---|---|
| JP | 2010049111 A | 3/2010 | |
| WO | 03083556 A2 | 10/2003 | |
| WO | 2005040866 A2 | 5/2005 | |
| WO | 2010-009447 A2 * | 1/2010 | A61B 3/16 |

OTHER PUBLICATIONS

Bass, Michael, "Optics Of The Eye", Handbook of Optics, vol. I—Capter Eye Models; Optical Society of America; 1995, McGraw-Hill, Inc.

Kingslake, Rudolf "Lens Design Fundamentals", Chapter 15: Eyepiece Design; 1978, Academic Press, Inc.; pp. 335-345.

Laikin, Milton "Lens Design", Chapter 10: Eyepieces; Library of Cngrett Cataloging-in-Publication Data; 1991, Marcel Dekker, Inc.; pp. 101-111.

Naumann, Helmut "Bauelemente der Optik: Taschenbuch der technischen Optik", Kapitel Objektive and Okulare für Fernrohre, 1992, pp. 337-341.

* cited by examiner

EYEPIECE

FIELD OF THE INVENTION

The present invention relates to an eyepiece, more particularly an eyepiece for an endoscope, a surgical microscope or another medical application.

BACKGROUND OF THE INVENTION

Eyepieces for medical and non-medical applications generally allow for positioning or displacement of the area perceived as in focus by the relaxed human eye and for a correction of axial ametropia (in particular hyperopia or farsightedness and myopia or nearsightedness) of an eye of a user of the eyepiece. Both parts together are commonly referred to as focusing and this is generally brought about by displacing the whole eyepiece or parts of the eyepiece parallel to the optical axis.

However, in addition to axial ametropia, the eyes of very many people exhibit an astigmatism. Due to a non-rotationally symmetric curvature of the cornea, a non-rotationally symmetric shape of the lens, an uneven contraction of the ciliary muscle and/or for different reasons, light rays emanating from an observed punctiform object are not imaged on the retina on a point, but rather in a line. Particularly the cornea and the lens of the eye have different refractive powers in different directions or in different planes perpendicular to the optical axis. The difference between the maximum refractive power and the minimum refractive power is specified in diopter. In order to characterize an astigmatism, the orientation of the plane of maximum refractive power or the orientation of the plane of minimum refractive power is furthermore specified; the two axes are orthogonal to one another in that significantly more common regular astigmatism.

Persons with not only a small astigmatism generally prefer not to remove their spectacles when looking through an eyepiece. However, this presumes a suitable design of the eyepiece. Moreover, the spectacles can be dirtied or the often high-quality, but mechanically sensitive coating thereof may be damaged in the case of the almost unavoidable contact with the eyepiece. As an alternative, some eyepieces have cylinder lenses which can be inserted or placed thereon. However, the eyepiece can then still only be used by a person or persons who perchance have the same astigmatism, and said persons can also only use said eyepiece without spectacles. These additional lenses are out of the question for practical reasons if an eyepiece is intended to be used by different persons or, alternately, with and without spectacles.

SUMMARY OF THE INVENTION

An object of the present invention consists in developing an improved eyepiece, in particular for medical applications, an improved endoscope, an improved surgical microscope and an improved control device for a surgical robot, which, in particular, can also be used by medical staff with an astigmatism.

This object is achieved by the invention.

An eyepiece comprises a focusing apparatus for positioning the area perceived as in focus by the relaxed human eye and for correcting axial ametropia of an eye of a user of the eyepiece, and a correction apparatus for adjustable correction of an astigmatism of an eye of a user of the eyepiece.

The eyepiece is provided and embodied, in particular, for use with an endoscope, a surgical microscope, any other microscope, a control apparatus for a surgical robot, field glasses, a telescope, a theodolite, a periscope, a telemeter, an Oechslemeter or magnifying spectacles, or as a component of one of the aforementioned optical instruments. The focusing apparatus is, in particular, embodied for displacing the plane or curved area, within which objects are perceived as in focus by the relaxed human eye or imaged in focus on the retina, and embodied for correcting hyperopia or farsightedness or myopia or nearsightedness.

The focusing apparatus in particular comprises a threaded or spindle drive or any other apparatus for manual or motor-driven movement of the whole eyepiece or of parts thereof in the direction parallel to the optical axis of the eyepiece.

The correction apparatus is, in particular, an apparatus for setting a cylindrical refractive power of the eyepiece or a difference between a maximum refractive power and a minimum refractive power of the eyepiece and for setting the orientation of the plane of maximum refractive power. The correction apparatus always remains completely on the eyepiece when setting the cylindrical refractive power or when setting the correction of an astigmatism. The setting of the cylindrical refractive power or the correction thereof therefore is not brought about by replacing or inserting or placing or taking down or removing a lens or any other light-refracting apparatus. The correction or the cylindrical refractive power can, in particular, be adjusted continuously. The correction apparatus comprises, in particular, one or more movable lenses or other optical elements for setting the corrective effect or the cylindrical refractive power.

The correction apparatus enables a simple and quick adaptation of the eyepiece to an astigmatism of a user. Acquisition and storage and insertion, placement, take down, removal or replacement of an additional lens or the like is not required. The eyepiece can be used by a plurality of persons with different astigmatisms and alternately by a person with and without spectacles; here, in each case all that is required is a new setting of the corrective effect.

In an eyepiece as described here, the correction apparatus in particular comprises two light-refracting apparatuses, which respectively have different refractive powers in different planes, the spacings of which are changeable or which are rotatable relative to one another.

Each one of the two or more light-refracting apparatuses comprises, in particular, one or more cylindrical lenses or other lenses, lens groups or lens systems which, in relation to different planes, have different refractive powers. Each one of the two or more light-refracting apparatuses can have an achromatic or apochromatic embodiment and, to this end respectively comprise, in particular, two or more transparent bodies made of different materials. An achromatic or apochromatic embodiment of the correction apparatus is furthermore possible by virtue of the fact that the two light-refracting apparatuses comprise different materials with, in particular, substantially reverse dependence of the refractive index on the wavelength.

The distance between the two light-refracting apparatuses of the correction apparatus can be modified, in particular, by moving or displacing one or both light-refracting apparatuses in the direction parallel to the optical axis of the eyepiece. In the case of a correction apparatus comprising three or more light-refracting apparatuses, the spacings of a plurality of light-refracting apparatuses of the correction apparatus can be modified by displacing or moving one, two or more light-refracting apparatuses in the direction parallel to the optical axis of the eyepiece. Alternatively, the cylindrical correction effect or the cylindrical refractive power can be set by rotating one or more of the light-refracting apparatuses about an axis, wherein the axis more particularly lies parallel to the optical axis of the eyepiece.

An eyepiece, as is described here, more particularly comprises a cylindrical lens with positive refractive power and a cylindrical lens with negative refractive power. The magnitudes of the refractive powers can be the same or different. In particular, the two surfaces of the cylindrical lenses respectively facing the other cylindrical lens have the same radii of curvature, wherein one of the two surfaces is convex and the other surface is concave. The cylindrical refractive power D of the combination of the two cylindrical lenses is approximately $D=(n-1)^2 \ast d/R^2$. Here, n is the identical refractive index of the two cylindrical lenses, d is the spacing between the two cylindrical lenses and R is the radius of curvature of the cylindrical surfaces, facing one another, of the cylindrical lenses. This equation applies to two cylindrical lenses, the sides of which facing away from one another being plane or planar. Deviating from this simple case, one or both surfaces facing away from one another may have cylindrical or any other curvature. Thus, in place of two cylinder lenses, use can be made of other lenses with cylindrical surfaces facing one another.

A complementary embodiment of the surfaces facing one another of two lenses that can be displaced with respect to one another enables a vanishing cylindrical refractive power when the two complementary surfaces touch one another. For an achromatic or apochromatic embodiment, the two lenses may comprise different materials with, in particular, substantially reverse dependence of the refractive indices on the wavelength.

Alternatively, the two light-refracting apparatuses of the correction apparatus may have two different refractive powers in terms of magnitude. In this case, the cylindrical refractive power of the correction apparatus can vanish in the case of the central spacing between the two light-refracting apparatuses and have different signs proceeding from this central spacing in the case of smaller and larger spacings.

By way of example, different refractive powers can be realized by different radii of curvature in the case where the two light-refracting apparatuses are made of the same material or by two different materials with different refractive indices in the case of the same radii of curvature.

In the case of an eyepiece, as is described here, the correction apparatus in particular comprises an interface between two media with different refractive indices, wherein the interface can be formed electrically, magnetically or by means of hydrostatic pressure.

The interface can be formed due to different properties of the two media which prevent mixture. By way of example, one medium is a hydrophilic or lipophobic liquid and the other medium is a hydrophobic or lipophilic liquid. Alternatively, one medium can be liquid and the other medium can be gaseous. The arrangement of the two media can be predetermined by different wetting properties of the various surface regions of a chamber which contains the two media. The interface between the two media can be formed by an electric and/or magnetic field, in particular due to different electric and/or magnetic properties of the two media. By way of example, an electric or magnetic field can be generated by means of electrodes or coils, respectively, within or outside of a chamber within which the two media are disposed.

Alternatively, the interface is formed by an optically transparent elastic membrane. Here, in particular, one of the two media is liquid and the other medium is liquid or gaseous. The optically transparent elastic membrane is deformed by virtue of, in particular, the difference in the hydrostatic pressures in the two media being modified.

As a result of a non-rotationally symmetric embodiment, for example an elongate-rectangular embodiment of the arrangement of the two media in a plane perpendicular to the optical axis of the eyepiece, it is possible to generate an embodiment of the interface between the two media which is substantially cylindrical, at least in a central region. The interface between the two media acts like a cylinder lens with an adjustable curvature.

Particularly an electric or magnetic influence of the formable interface between the two media renders possible a simple and robust control of the cylindrical refractive power without requiring a linear drive or any other drive apparatus with movable parts.

In an eyepiece, as is described here, the correction apparatus is rotatable about the optical axis of the eyepiece in particular.

In particular, the whole eyepiece is rotatable about the optical axis. Alternatively, e.g. the aforementioned cylinder lenses or a container, in which the aforementioned two media with different refractive indices are disposed, is/are rotatable about the optical axis of the eyepiece.

An eyepiece, as is described here, furthermore comprises, in particular, an operating apparatus for setting a cylindrical refractive power.

By way of example, the operating apparatus is disposed in a ring-shaped manner and symmetrically with respect to the optical axis of the eyepiece. In particular, the operating apparatus is rotatable about the optical axis of the eyepiece and coupled to the correction apparatus by a threaded or spindle drive.

An eyepiece, as is described here furthermore comprises, in particular, a further operating apparatus for setting the orientations of maximum and minimum refractive powers of the correction apparatus.

By way of example, the further operating apparatus is disposed in a ring-shaped manner and symmetrically with respect to the optical axis of the eyepiece and rotatable about the optical axis of the eyepiece and directly or indirectly mechanically connected to the correction apparatus.

In particular, scales for the cylindrical refractive power and for an angle describing the orientations of the maximum and minimum refractive power are respectively disposed on the operating apparatus and on the further operating direction.

In the case of an eyepiece, as is described here, the correction apparatus, in particular, forms a proximal light-emergence surface of the eyepiece.

In particular, the correction apparatus forms a proximal coverslip or a window component that closes off the eyepiece in the proximal direction. Expressed differently, the coverslip or the window component is a part of the correction apparatus. To this end, for example, one of the aforementioned cylinder lenses or a light-emergence window of a container, in which at least one of the two aforementioned media with different refractive indices is disposed, is simultaneously embodied as light-emergence window of the eyepiece. This enables an arrangement of the correction apparatus very far in the proximal direction and therefore, overall, a very compact design of the eyepiece.

An eyepiece, as it is described here, furthermore comprises, in particular, a motor-driven drive apparatus for a motor-driven adjustment of the correction apparatus.

The eyepiece comprises, in particular, a motor-driven drive apparatus for adjusting the cylindrical refractive power and a motor-driven drive apparatus for adjusting the orientation of the maximum and of the minimum refractive power. A motor-driven drive apparatus in particular comprises a stepper motor or any other electric motor, an ultrasonic motor or a piezo-motor.

A motor-driven drive apparatus can enable a quick adjustment of the corrective effect of the correction apparatus of the eyepiece. The motor-driven drive apparatuses can be coupled to a camera and to an apparatus for facial, iris or retina identification, an RFID receiver or any other identification apparatus, as well as to a database, in which parameters which describe the astigmatism and, optionally, further ametropias of one or more users are stored. This can enable an automatic adjustment of the eyepiece to the user as soon as the latter approaches the eyepiece.

An endoscope comprises an eyepiece, as it is described here.

An endoscope with an eyepiece, as is described here, has, in particular, an astigmatism which is dependent on the refractive index of a medium, in which the distal end of the endoscope is disposed.

Medical endoscopes in particular are often operated alternately in air, carbon dioxide or another gas which has a refractive index close to 1, and in water or another aqueous liquid. Particularly if the distal light-entry window of the endoscope is non-spherical, for example if it has the form of a section of a circular cylinder, this results in an astigmatism of the endoscope which is dependent on the refractive index of the medium in which the distal light-entry window is disposed.

The correction apparatus of the eyepiece can also enable a correction of the astigmatism of the endoscope which is dependent on the refractive index of the medium.

An endoscope with an astigmatism which is dependent on the refractive index of a medium furthermore comprises, in particular, an operating apparatus for changing the cylindrical refractive power of the correction apparatus by a predetermined value, which corresponds to the difference between the astigmatism of the endoscope when the distal end is disposed in air and the astigmatism of the endoscope when the distal end is disposed in water.

The operating apparatus allows the corrective effect of the correction apparatus to be switched between the two corrective effects required when arranging the distal end of the endoscope in air or in water. Settings on the eyepiece which are related to the astigmatism of the eye of the user can thus be maintained.

A surgical microscope comprises an eyepiece, as is described here.

A control device for a surgical robot comprises an eyepiece, as is described here.

A surgical robot is a device for performing medical, in particular surgical, interventions by means of servomotors. Movements of instruments and tools, or of the surgical robot itself are not driven directly or indirectly by hand, but are generated by servomotors. The surgical robot and the drive apparatuses thereof are controlled by medical staff, wherein a computer can prepare and filter the control commands generated by the surgical staff and check said commands in respect of maintaining safety rules, before the control signals or modified control signals are forwarded to the drive apparatuses of the surgical robot.

The control of a surgical robot generally requires high levels of concentration. In order to keep bothersome optical influences away from the medical staff, and in order to impart a three-dimensional impression of the operating field on the medical staff, two eyepieces can be provided on a control device for a surgical robot.

A surgical microscope or control device, as is described here, comprises, in particular, a tray apparatus for holding spectacles.

A member of medical staff with ametropia, who uses the surgical microscope or the control device, may put down his spectacles directly on the surgical microscope or on the control device.

BRIEF DESCRIPTION OF THE DRAWINGS

In the following, embodiments will be explained in more detail on the basis of the attached figures. In detail.

DETAILED DESCRIPTION OF THE INVENTION

Figure 1:
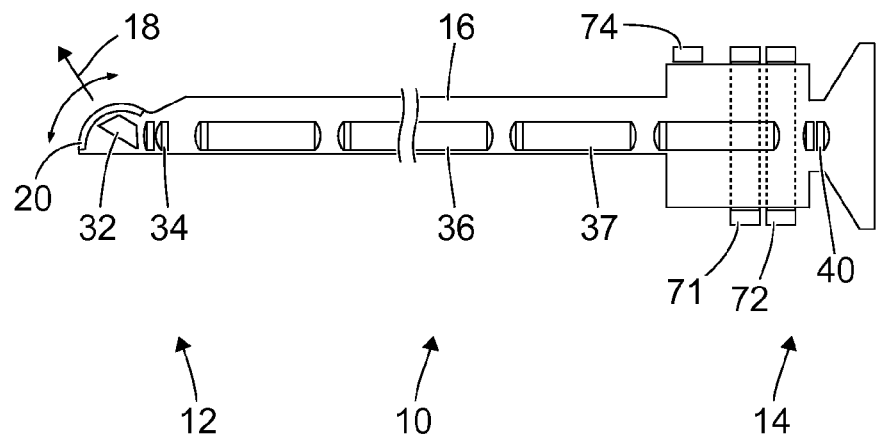
FIG. 1 shows a schematic illustration of an endoscope.

FIG. 1 shows a schematic illustration of an endoscope 10 comprising a distal end 12 and a proximal end 14. A straight and rigid shank 16 extends from the distal end 12 to the proximal end 14 of the endoscope 10. The direction of view 18 of the endoscope 10 can be adjusted within an angular range indicated in FIG. 1 by a bent double-headed arrow.

The endoscope 10 and the features thereof described above are substantially indicated by contours in FIG. 1. By contrast, the optical apparatuses described below are indicated in a side view. Depicted here in projection on the plane of the drawing are not only the external contours of the optical apparatuses, as become visible in the case of a section along a plane containing the optical axis, but also edges which arch out of the plane of the drawing, in particular with a circular arc shape. It is possible to identify, in particular, circular arc-shaped edges between arched light-entry surfaces or light-emergence surfaces on the one hand and cylindrical barrel surfaces (parallel to the optical axis) on the other hand as straight lines orthogonal to the longitudinal axis of the endoscope 10 since these circular arc-shaped edges lie in planes orthogonal to the optical axis and therefore also orthogonal to the longitudinal axis of the endoscope 10 and to the plane of the drawing. Furthermore, the likewise circular arc-shaped edges of interfaces between elements cemented together can be identified as straight lines.

At the distal end 12, the endoscope 10 comprises a window component 20 made of a material which is transparent, in particular, to light within the wavelength range visible to the human eye or which has the highest possible transmission. The window component 20 has the form of a section of a circular cylinder barrel, wherein the cylinder axis of the circular cylinder barrel is orthogonal to the optical axis of further optical apparatuses of the endoscope 10, orthogonal to the longitudinal axis of the shank 16, orthogonal to the direction of view 18 of the endoscope and orthogonal to the plane of the drawing.

A swivel prism 32 is disposed directly proximally to, and downstream in the direction of light propagation of, the window component 20. The swivel prism 32 in particular has the form of a dove prism and can swivel about a swivel axis (not depicted here) orthogonal to the plane of the drawing of FIG. 1 in order to set the direction of view 18.

An objective 34 made of one or more lenses or any other imaging apparatus for generating an intermediate image of an object observed by means of the endoscope 10 is disposed downstream of the swivel prism 32 in the direction of light propagation. A rod lens system made of a plurality of rod lenses 36, 37 or any other relay lens system for transmitting the intermediate image generated by the objective 34 to the distal end 14 of the endoscope 10 is disposed proximally and downstream of the objective 34 in the direction of light propagation in the shank 16.

An eyepiece 40 for generating a virtual image which can be registered by the human eye is disposed proximally and downstream of the rod lens system 36, 37 in the direction of light propagation. In particular, the eyepiece 40 comprises a plurality of lenses and simultaneously hermetically seals the endoscope 10 at the proximal end 14.

As a result of its non-spherical but rather circular cylinder barrel-shaped design, the window component 20 at the distal end 12 of the endoscope 10 generates imaging errors or aberrations which increase with increasing ratio of the wall thickness to the radius of curvature of the window component 20 and with increasing diameter of a light beam registered by means of the swivel prism, the objective 34, the rod lens system 36, 37 and the eyepiece 40. In particular, the window component 20 has an axial astigmatism.

The eyepiece 40 is embodied for correcting an astigmatism of an eye of a user of the eyepiece. To this end, in particular, the eyepiece comprises a correction apparatus and further features and properties, which are described in more detail below with reference to FIGS. 2 to 7. In particular, the correction apparatus is furthermore suited and embodied to correct an astigmatism of the endoscope 10 arising from the design of the window component 20, which is not rotationally symmetric in relation to the direction of view 18.

Operating apparatuses 71, 72, 74, by means of which the eyepiece 40 can be adjusted, are provided at the proximal end 14 of the endoscope 10. In particular, a cylindrical refractive power of the eyepiece 40 can be set by means of a first operating apparatus 71. In particular, the orientations of the planes containing the optical axis of the eyepiece, in which the eyepiece has a maximum and a minimum refractive power, respectively, can be set by means of a second operating apparatus 72. In particular, the third operating apparatus 74 is embodied to modify the cylindrical refractive power of the eyepiece 40 by a value which corresponds to the difference between the cylindrical refractive powers of the light-entry surface of the window component in air and in water.

Figure 2:
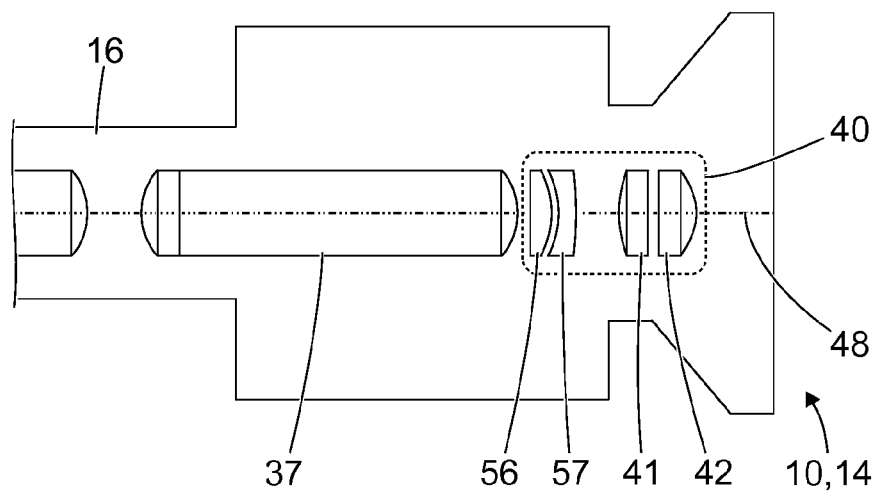
FIG. 2 shows a schematic illustration of an eyepiece.

FIG. 2 shows a schematic sectional illustration of an eyepiece 40 at the proximal end 14 of an endoscope 10, which is only indicated in the FIG. 2. The plane of the drawing and the type of representation, in particular the type of representation of optical elements, correspond to those in the FIG. 1. In particular, the endoscope 10 has features and properties which are illustrated above on the basis of FIG. 1.

The eyepiece 40 is disposed at the proximal end 14 of the endoscope 10 in order to generate a virtual image, which can be registered by the human eye, of an intermediate image generated by a rod lens 37. The eyepiece 40 comprises a first, distal lens 41 and a second, proximal lens 42, which are in each case spherical or at least rotationally symmetrical in relation to the optical axis 48 of the eyepiece 40. The second, proximal lens 42 hermetically seals the eyepiece in the proximal direction. As an alternative to the hermetically sealed closure, provision is made for a transparent window component with two plane and parallel surfaces. An advantage of such a window component may be that it need not be adjusted in relation to the optical axis 48 of the eyepiece.

Furthermore, the eyepiece 40 comprises a correction apparatus with a first, distal correction lens 56 and a second, proximal correction lens 57. Each correction lens 56, 57 respectively has two different refractive powers in two different planes containing the optical axis 48 of the eyepiece 40. In particular, each one of the two correction lenses 56, 57 is embodied as a cylinder lens.

A cylinder is a body which is delimited by two plane and parallel surfaces, which are also referred to as base and top surfaces, and by a lateral or cylinder surface. The lateral or cylinder surface is formed by parallel straight lines, which connect mutually corresponding points on the edges of the plane surfaces. Thus, a cylinder is created by displacing a planar surface or a curve along a straight line not lying in the plane of the surface or curve. Base surface and top surface can be circular or have any other form. If the base surface and cover surface are circular, the cylinder is a circular cylinder. If the straight lines forming the lateral surface or cylinder surface are perpendicular to the plane surfaces, the cylinder is referred to as a right cylinder.

A cylinder axis of a cylinder refers to any straight line which is parallel to the straight lines that form the lateral or cylinder surface. The cylinder axis specifies the direction in which the cylinder is translation invariant within certain limits. The cylinder axis of a circular right cylinder is the straight line on which the center points of base and cover surface lie. The circular right cylinder is rotationally symmetric in relation to this axis of symmetry.

In a cylinder lens, the plane and parallel base and top surface of the cylinder have no role and are, in particular, removed or modified by grinding or in any other way. The light-entry surface and the light-emergence surface are formed by parts of the lateral surface of a cylinder, the cylinder axis of which, in particular, is orthogonal to the optical axis of the optical apparatus of which the cylinder lens is a part.

The correction lenses 56, 57 are, in particular, cylinder lenses, the cylinder axes of which are orthogonal to the optical axis 48 of the eyepiece 40 and orthogonal to the plane of the drawing of FIG. 2. The correction lenses 56, 57 have rectangular contours (in relation to a plane orthogonal to the optical axis 48).

In the embodiment, indicated in FIG. 2, of the correction lenses 56, 57 as cylinder lenses with cylinder axes orthogonal to the plane of the drawing in FIG. 2, each correction lens 56, 57 has a vanishing refractive power (refractive power=0 dpt) in a plane, perpendicular to the plane of the drawing in FIG. 2, containing the optical axis 48 of the eyepiece 40.

In the embodiment of the correction lenses 56, 57, indicated in FIG. 2, the light-emergence surface of the first correction lens 56, facing the second correction lens 57, and the light-entry surface of the second correction lens 57, facing the first correction lens 56, have the same, in particular circular cylindrical, design. The first correction lens 56 is convex; the second correction lens 57 is concave. If the surfaces facing one another of the correction lenses 56, 57 touch one another, as approximately indicated in FIG. 2, the refractive power of the two surfaces facing one another of the correction lenses 56, 57 is zero. If the two surfaces facing one another of the correction lenses 56, 57 are at a distance from one another, they have, in combination, a cylindrical refractive power that differs from zero.

The light-entry surface of the first correction lens 56, facing away from the second correction lens 57, and the light-emergence surface of the second correction lens 57, facing away from the first correction lens 56, can respectively be plane or planar, or else curved. FIG. 2 indicates, in an exemplary manner, a slight cylindrical curvature of the surface of the second correction lens 57 facing away from the first correction lens 56.

Deviating from the illustration in FIG. 2, the light-entry surface of the first correction lens 56, facing away from the second correction lens 57, and the light-emergence surface of the second correction lens 57, facing away from the first correction lens 56, can respectively have the form of a section of a circular cylinder, of any other cylinder, of a sphere surface, of a surface of a rotational ellipsoid, of a surface of a torus or any other form.

The whole eyepiece 40 can be moved, either manually or in a motor-driven manner, in the direction parallel to the optical axis 48 of the eyepiece 40 by means of an operating apparatus (not depicted in FIG. 1) and a spindle drive, or by means of any other apparatus (not depicted in the figures). Alternatively, one or both spherical lenses 41, 42 of the eyepiece 40 can be moved, either manually or in a motor driven manner, parallel to the optical axis 48 of the eyepiece 40 by means of a spindle drive or in any other way. By means of suitable positioning of the whole eyepiece 40 or of one or both spherical lenses 41, 42 of the eyepiece 40, an image registered by the human eye through the eyepiece 40 or generated on the retina of the human eye can be put into focus. In the process, axial ametropia of the eye is, in particular, also corrected.

An astigmatism of the eye of the user of the endoscope 10 and, where applicable, an astigmatism of the endoscope 10 cannot yet be corrected by only positioning the whole eyepiece 40 or one or both spherical lenses 41, 42. In order to correct an astigmatism of the eye of the user and/or in order to correct an astigmatism of the endoscope 10, the distance between the correction lenses 56, 57 can be modified by virtue of at least one of the two correction lenses 56, 57 being movable parallel to the optical axis 48 of the eyepiece 40. Furthermore, both correction lenses 56, 57 together, or the whole eyepiece 40, can be rotated about the optical axis 48 in order to set the orientations of the planes of the maximum and minimum refractive power.

The eyepiece 40 and its constituents are coupled to the operating apparatuses 71, 72, 74 depicted in FIG. 1 by mechanical means and/or by means of magnets which enable coupling through a hermetically sealed sleeve. In particular, the first operating apparatus 71 for setting the cylindrical refractive power is coupled to the correction lenses 56, 57 in such a way that the spacing of the correction lenses 56, 57 can be modified by means of the first operating apparatus 71. The second operating apparatus 72 is, in particular, coupled to the correction lenses 56, 57 in such a way that the correction lenses 56, 57, or the whole eyepiece 40, can be rotated about the optical axis 48 of the eyepiece 40 by means of the second operating apparatus 72. The optional third operating apparatus 74 is, in particular, embodied as a mechanical switch or can be displaced or rotated between two positions which, for example, are defined by latches. The third operating apparatus 74 is, in particular, coupled to the correction lenses 56, 57 in such a way that the cylindrical refractive power of the correction apparatuses 56, 57 can be modified by a predetermined refractive power, corresponding to the difference of the astigmatism of the endoscope 10 when the distal end 12 (cf. FIG. 1) is disposed in air or water, by means of the third operating apparatus 74.

Figure 3:
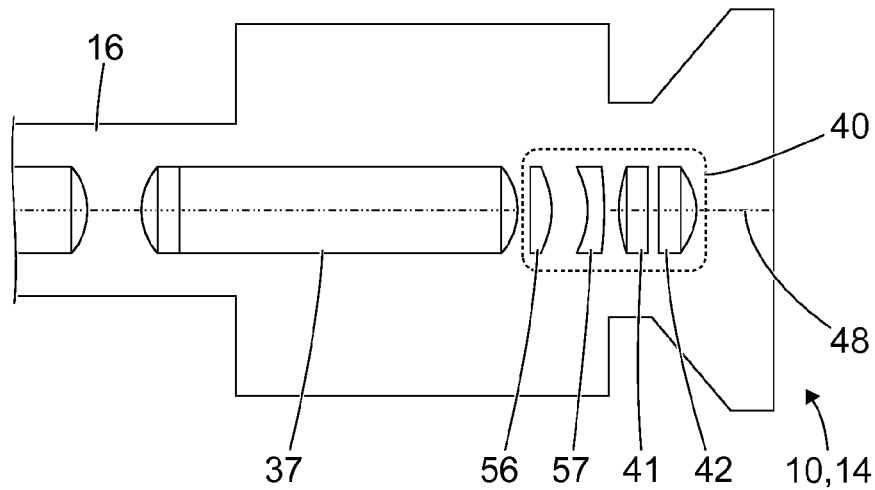
FIG. 3 shows a further schematic illustration of the eyepiece from FIG. 2.

FIG. 3 shows a further schematic illustration of the eyepiece 40 from FIG. 2. The plane of the drawing and the type of representation correspond to those in FIGS. 1 and 2. FIG. 3 shows the eyepiece 40 in a situation or configuration where the distance between the correction lenses 56, 57 has increased compared to the situation or configuration in FIG. 2. While the cylindrical refractive power of the combination of the two correction lenses 56, 57 is small in the configuration depicted in FIG. 2, it is larger in the configuration depicted in FIG. 3. Many different cylindrical refractive powers can be set within a predetermined interval by displacing the second correction lens 57 relative to the first correction lens 56.

Figure 4:
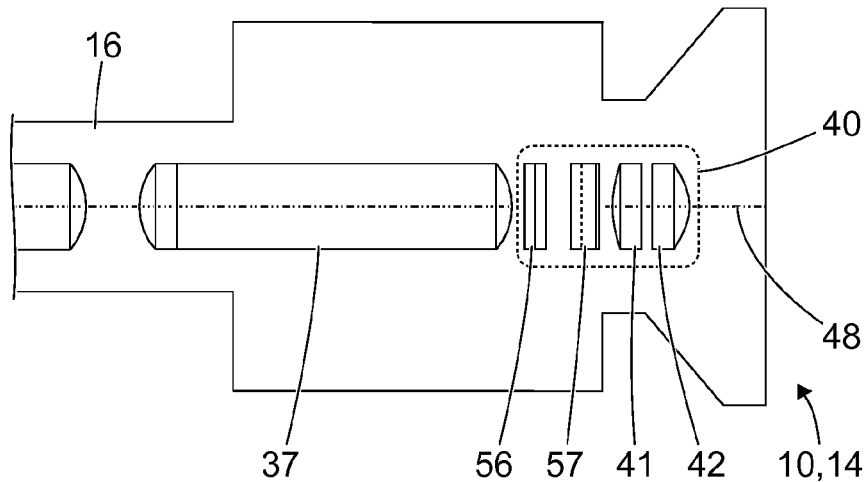
FIG. 4 shows a further schematic illustration of the eyepiece from FIGS. 2 and 3.

FIG. 4 shows a further schematic illustration of the eyepiece 40 from FIGS. 2 and 3. The plane of the drawing is orthogonal to the planes of the drawings in FIGS. 1 to 3. In relation to the plane of the drawing in FIG. 4, the combined refractive power of the two mutually facing cylindrically curved surfaces of the correction lenses 56, 57 is zero. The common refractive power of the two mutually facing cylindrically curved surfaces of the correction lenses 56, 57 only differs from zero, and can only be set, in the planes of the drawings of FIGS. 2 and 3.

Figure 5:
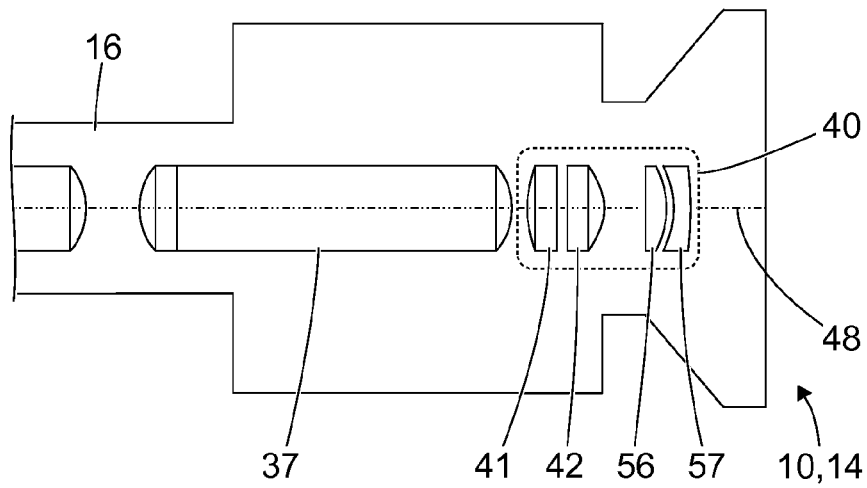
FIG. 5 shows a schematic illustration of a further eyepiece.

FIG. 5 shows a schematic illustration of a further eyepiece 40 at the proximal end 14 of an endoscope 10 only indicated in FIG. 5. The plane of the drawing and the type of representation correspond to those in FIGS. 1 to 3. In terms of some features and properties, the eyepiece 40 is similar to the eyepiece illustrated above on the basis of FIGS. 2 to 4. The following text describes features and properties of the eyepiece 40, by means of which it differs from the one illustrated above on the basis of FIGS. 2 to 4.

The eyepiece depicted in FIG. 5 differs from the eyepiece illustrated above on the basis of FIGS. 2 to 4 in that, in particular, the two correction lenses 56, 57 are disposed proximately to the two spherical lenses 41, 42. While, in particular, the proximal spherical lens 42 hermetically seals the eyepiece 40 in the proximal direction in the eyepiece 40 illustrated on the basis of FIGS. 2 to 4, this object is assumed, in particular, by the proximal correction lens 57 in the eyepiece depicted in FIG. 5.

Deviating from the illustrations on the basis of FIGS. 2 to 5, the two correction lenses 56, 57 can, in particular, be disposed between the two spherical lenses 41, 42. Deviating from the illustrations on the basis of FIGS. 2 to 5, provision can be made for more than two spherical lenses and/or for more than two correction lenses 56, 57.

Figure 6:
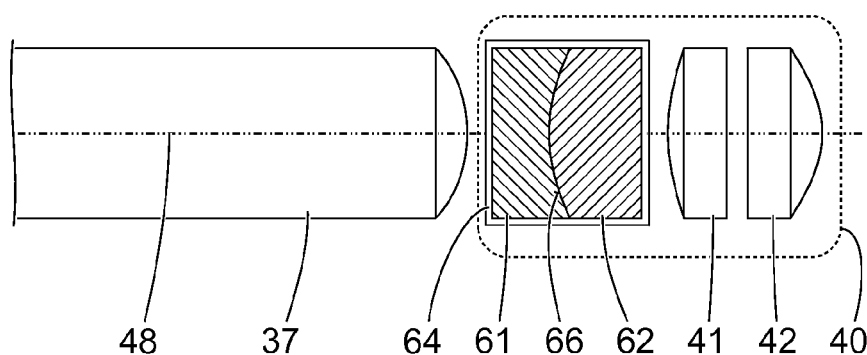
FIG. 6 shows a schematic illustration of optical apparatuses of a further eyepiece.

FIG. 6 shows a schematic illustration of a further eyepiece 40 which, in terms of some features and properties, is similar to the eyepieces illustrated above on the basis of FIGS. 2 to 5. The plane of the drawing corresponds to the planes of the drawings in FIGS. 1 to 3 and 5; the type of representation corresponds to that in FIGS. 1 to 5, wherein, however, contours of an endoscope are not indicated. The following text describes features and properties of the eyepiece 40, by means of which it differs from the eyepieces illustrated above on the basis of FIGS. 2 to 5.

The eyepiece 40 depicted in FIG. 6 differs from the eyepieces illustrated above on the basis of FIGS. 2 to 5 in that, in particular, provision is made for a liquid lens, comprising a first medium 61 and a second medium 62 in a chamber 64, in place of two correction lenses, the spacing of which can be set. The media 61, 62 and at least the wall sections of the chamber 64 provided for the passage of light are optically transparent. The media 61, 62 have different refractive indices, and so light is refracted at the interface 66 between the media 61, 62.

The interface 66 between the media 61, 62 can be formed by an optically transparent and mechanically elastic membrane. Alternatively, the interface 66 can be due to low miscibility of the two media 61, 62. By way of example, one of the two media 61, 62 is liquid and the other is gaseous, or one of the two media 61, 62 is lipophilic or hydrophobic and the other one is hydrophilic or lipophobic.

In particular, the two media 61, 62 have the same or similar mass density. In this case, gravity and, where applicable, an accelerated movement has no, or only little, influence on the media 61, 62, and the form of the interface 66 does not depend, or only depends a little, on the orientation of the eyepiece 40 in Earth's gravitational field and nor is it changed, or it is only changed slightly, by tremors.

The two media 61, 62 have different electric properties, for example different values of permittivity. Electrodes for generating electrostatic fields (not depicted in FIG. 6) are provided on or in the chamber 64, by means of which electrostatic fields the form of the interface 66 between the media 61, 62 can be influenced.

Alternatively, the media 61, 62 have different magnetic properties and one or more coils for generating a magnetic field are provided on the chamber 64, by means of which magnetic fields the form of the interface 66 between the media 61, 62 can be influenced.

Alternatively or additionally, the chamber 64 has a fluid connection to one or more pressure sources or equalizing containers, which enable supply or removal of one or both media 61, 62 out of the chamber or into the chamber 64 for forming the interface 66.

If the interface 66 between the two media 61, 62 is formed by a membrane, this membrane is, in particular, stiffened in one direction or has anisotropic elastic properties for other reasons. What the anisotropic elastic properties bring about is that the membrane only or predominantly curves or arches in one direction and at least approximately assumes the shape of a cylinder barrel. Alternatively, the membrane can, for example, be guided appropriately or clamped in a long and thin frame in order to cause substantially cylindrical arching.

If the interface 66 between the two media 61, 62 is due to a low miscibility of the two media 61, 62, a cylindrical or substantially cylindrical arching of the interface 66 can be brought about, in particular, by the form or shape of the chamber 64 (for example long and narrow in a projection onto a plane orthogonal to the optical axis 48) and/or by the form of the boundary between surfaces which are wetted differently by the two media 61, 62 and/or by the arrangement and the form or shape of electrodes or coils.

Figure 7:
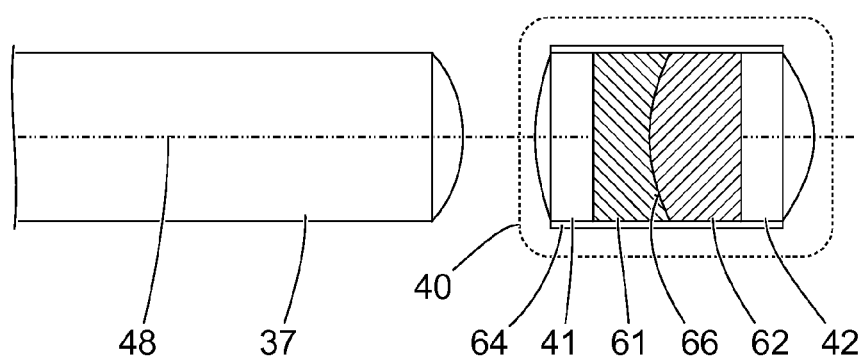
FIG. 7 shows a schematic illustration of optical apparatuses of a further eyepiece.

FIG. 7 shows a schematic illustration of a further eyepiece 40 which, in terms of some features and properties, is similar to the eyepieces illustrated above on the basis of FIGS. 2 to 6 and, in particular, to the eyepiece illustrated on the basis of FIG. 6. The plane of the drawing corresponds to the planes of the drawings in FIGS. 1 to 3, 5 and 6; the type of representation corresponds to that in FIG. 6. The following text describes features and properties of the eyepiece 40, by means of which it differs from the one illustrated above on the basis of FIG. 6.

The eyepiece 40 depicted in FIG. 7 differs from the eyepiece illustrated above on the basis of FIG. 6 in that, in particular, the two media 61, 62 are disposed between the spherical lenses 56, 57. The chamber 64 is formed by a tubular component which is sealed at both ends by the spherical lenses 56, 57. Thus, the spherical lenses 56, 57 form the light-entry window and the light-emergence window of the chamber 64. This design is particularly compact, has particularly few surfaces which, firstly, are to be tempered and, secondly, could dirty, and has particularly few interfaces at which undesired reflections could occur.

In the embodiments illustrated on the basis of FIGS. 1 to 7, lenses 41, 42, 56, 57 are provided with curved light-refracting surfaces. Alternatively or additionally, provision can be made for other diffractive optical elements or gradient-index lenses. In particular, gradient-index lenses with a radial gradient can replace the spherical lenses 41, 42 and gradient-index lenses with an axial gradient can replace the correction lenses 56, 57.

By way of example, a gradient-index lens is produced by virtue of a glass rod with initially a homogeneous refractive index being heated in a salt bath. Ions from the salt bath diffuse into the glass rod and ions from the glass rod diffuse into the salt bath. As a result, some of the ions in the glass rod are exchanged or replaced. Exchanging ions in the glass modifies the refractive index of the glass. Since more ions are exchanged near the surface of the glass rod than in the interior thereof, a gradient in the refractive index is created. In a circular cylindrical glass rod, a refractive index increasing quadratically or increasing approximately quadratically in the outward direction from the cylinder axis is typical. Depending on the replaced and replacing ions, the refractive index can be increased or reduced.

A circular cylindrical glass rod with a refractive index increasing or decreasing from the inside to the outside is generally used in such a way that the cylinder axis thereof and the optical axis coincide. Alternatively, such a glass rod can be processed to form an optical component with a different geometry, in particular by grinding or sawing. By way of example, a glass plate with two plane and parallel surfaces and a refractive index varying in only one direction is manufactured by virtue of a layer being cut out of the glass rod or by virtue of material being ablated from the glass rod in such a way that this layer remains. The layer contains, in particular, the cylinder axis. The two plane and parallel surfaces are parallel to the cylinder axis and serve as light-entry surface and light-emergence surface. In particular, the glass plate is used or disposed in such a way that the cylinder axis and the two parallel light-entry and light-emergence surfaces are respectively orthogonal to the optical axis. In this arrangement, the glass plate represents a gradient-index cylinder lens which, in particular, can replace or complement the correction lenses 56, 57 of the embodiments illustrated on the basis of FIGS. 1 to 5.

A gradient-index cylinder lens in the form of a transparent plate with a refractive index varying in one direction only can alternatively be produced differently. In particular, a glass plate with initially a homogeneous refractive index is immersed into molten salt, wherein the immersion depth is a function of time. Here, the two plane and parallel surfaces of the glass plate are orthogonal to the liquid level of the molten glass.

If the glass plate has a low thickness, diffusion in the direction parallel to the two plane and parallel surfaces of the glass plate can be ignored. In this approximation, the number of exchanged ions at each location within the glass plate is proportional to the dwell time of this location in the molten salt.

By way of example, immersing the glass plate into the molten salt and removing the glass plate from the molten salt with in each case a constant velocity causes a refractive index which is an affine linear function of a coordinate. The gradient of the refractive index is constant.

It is possible to obtain an almost arbitrary (monotonic) spatial dependence of the refractive index by immersion into the molten salt and removal from the molten salt with a non-constant velocity. By virtue of a rectangular glass plate being immersed sequentially, initially starting from one edge and, after a rotation through 180°, starting from the opposite edge, into the molten salt with in each case velocity varying quadratically, it is possible to obtain a refractive index which, proceeding from a central axis, respectively increases quadratically in both directions. Using a different time dependence of the immersion depth and the immersion velocity, it is possible to realize an almost arbitrary spatial dependence of the refractive index.

The eyepieces illustrated above on the basis of FIGS. 2 to 7 can be used in, or on, endoscopes, wherein, in each case, the eyepiece is, in particular, permanently connected to the endoscope. Alternatively, an eyepiece with the features and properties illustrated above on the basis of FIGS. 2 to 7 can be provided as part of a surgical microscope, any other microscope, field glasses, a telescope, a theodolite, a periscope, a telemeter, an Oechslemeter, magnifying spectacles or any other optical instrument for medical or non-medical applications, or provided for use with one of the aforementioned instruments.

Figure 8:
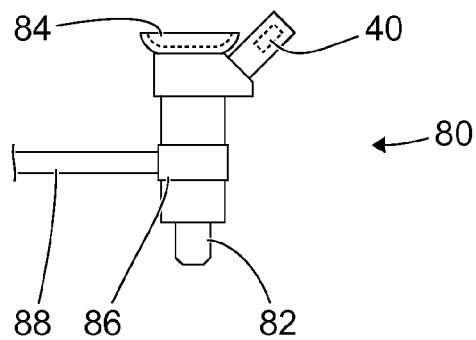
FIG. 8 shows a schematic illustration of a surgical microscope.

FIG. 8 shows a schematic illustration of a surgical microscope 80 with an objective 82. An eyepiece 40 indicated by a dashed line is disposed in a tube. The eyepiece 40 is one of the eyepieces illustrated above on the basis of FIGS. 2 to 7 or has features and properties which were illustrated above on the basis of FIGS. 2 to 7. The surgical microscope 80 may comprise two eyepieces 40 in order to enable medical staff a simultaneous view through the surgical microscope 80 with both eyes, or even optionally to enable stereoscopy.

Furthermore, the surgical microscope 80 comprises a tray 84 for spectacles. The tray 84 is disposed, in particular, in the vicinity of the eyepiece or eyepieces 40, has the shape of a flat shell and holds the spectacles of a member of the medical staff when he or she wishes to look into the surgical microscope 80 without spectacles.

The surgical microscope 80 furthermore comprises a stand connector 86 for the detachable mechanical connection between the surgical microscope 80 and a stand 88. Within predetermined limits, the stand 88 enables an arbitrary or largely arbitrary arrangement and orientation of the surgical microscope 80 over an operating field.

Figure 9:
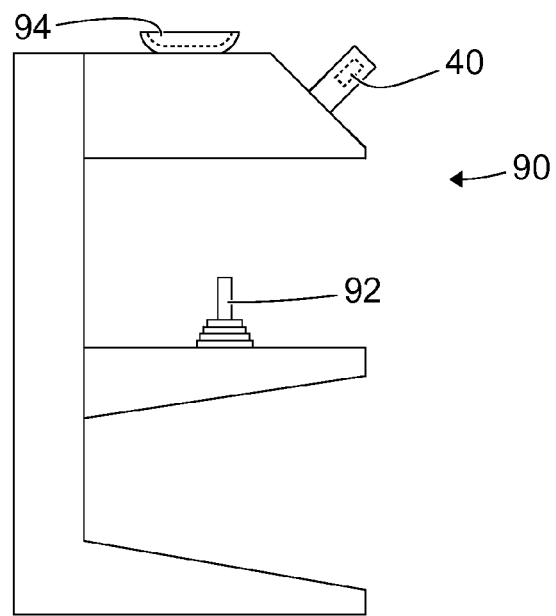
FIG. 9 shows a schematic illustration of a control device.

FIG. 9 shows a schematic illustration of a control device 90 for a surgical robot. Devices which, driven by servo drives, can undertake medical interventions are referred to as surgical robots. Until now, a surgical robot was controlled, at least from time to time and at least indirectly, by medical staff. The intervention can be monitored at the control device 90 by looking through one or two eyepieces 40, as illustrated above on the basis of FIGS. 2 to 7. In particular, a stereoscopic image is generated by the eyepieces 40, said image being acquired by a camera on the surgical robot or in the vicinity thereof. In order to control the servomotors, one, two or more operating apparatuses 92 are available, which, for example, can be embodied as joysticks or the like.

A tray 94 for spectacles is provided in the vicinity of the eyepiece or eyepieces 40. The tray 94, in particular, has the shape of a shell for holding the spectacles of a member of the medical staff when he or she wishes to look into the eyepiece or eyepieces 40 without spectacles.

The invention claimed is:

1. An eyepiece comprising:
   a focusing apparatus for positioning an area perceived as in focus by a relaxed human eye and for correcting axial ametropia of an eye of a user of the eyepiece;
   a correction apparatus for adjustable correction of an astigmatism of the eye of the user of the eyepiece, the correction apparatus having two light-refracting apparatuses aligned along an optical axis of the eyepiece, the two light-refracting apparatuses being separated by a distance that can be changed by moving at least one of the two light-refracting apparatuses in a direction parallel to the optical axis;
   wherein the correction apparatus is rotatable about an optical axis of the eyepiece.

2. The eyepiece according to claim 1, wherein the correction apparatus comprises an interface between two media with different refractive indices, wherein the interface can be formed electrically, magnetically or by means of hydrostatic pressure.

3. The eyepiece according to claim 1, further comprising:
   an operating apparatus for setting a cylindrical refractive power.

4. The eyepiece according to claim 3, further comprising:
   a second operating apparatus for setting an orientation of maximum and minimum refractive powers of the correction apparatus.

5. The eyepiece according to claim 1, wherein the correction apparatus forms a proximal light-emergence surface of the eyepiece.

6. A surgical microscope comprising the eyepiece according to claim 1.

7. A control device for a surgical robot comprising the eyepiece according to claim 1.

8. The eyepiece according to claim 1, wherein the correction apparatus comprises two light-refracting apparatuses, which respectively have different refractive powers in different planes; and wherein the two light-refracting apparatuses are rotatable relative to one another.

9. An observing system comprising the eyepiece of claim 1, wherein a natural image of a patient is formed on the eye of the user.

10. A medical device, comprising:
    an endoscope having an eyepiece;
    the eyepiece having a focusing apparatus for positioning an area perceived as in focus by a relaxed human eye and for correcting axial ametropia of an eye of a user of the eyepiece;
    a correction apparatus having a cylindrical refractive power for adjustable correction of an astigmatism of the eye of the user of the eyepiece.

11. The medical device according to claim 10, wherein the endoscope has an astigmatism which is dependent on a refractive index of a medium, in which a distal end of the endoscope is disposed.

12. The medical device according to claim 11, further comprising:
    an operating apparatus for changing the cylindrical refractive power of the correction apparatus by a predetermined value, the value corresponding to a difference between a first astigmatism of the endoscope when the distal end is disposed in air and a second astigmatism of the endoscope when the distal end is disposed in water.

13. An eyepiece comprising:
a focusing apparatus for positioning an area perceived as in focus by a relaxed human eye and for correcting axial ametropia of an eye of a user of the eyepiece;
a correction apparatus for adjustable correction of an astigmatism of the eye of the user of the eyepiece, the correction apparatus having two light-refracting apparatuses aligned along an optical axis of the eyepiece, the two light-refracting apparatuses being separated by a distance that can be changed by moving at least one of the two light-refracting apparatuses in a direction parallel to the optical axis;
wherein the correction apparatus comprises an interface between two media with different refractive indices, wherein the interface can be formed electrically, magnetically or by means of hydrostatic pressure.

14. An eyepiece comprising:
a focusing apparatus for positioning an area perceived as in focus by a relaxed human eye and for correcting axial ametropia of an eye of a user of the eyepiece;
a correction apparatus for adjustable correction of an astigmatism of the eye of the user of the eyepiece, the correction apparatus having two light-refracting apparatuses aligned along an optical axis of the eyepiece, the two light-refracting apparatuses being separated by a distance that can be changed by moving at least one of the two light-refracting apparatuses in a direction parallel to the optical axis;
wherein the correction apparatus comprises two light-refracting apparatuses, which respectively have different refractive powers in different planes; and wherein the two light-refracting apparatuses are rotatable relative to one another.

* * * * *